US011185567B2

(12) United States Patent
Fauquert et al.

(10) Patent No.: US 11,185,567 B2
(45) Date of Patent: Nov. 30, 2021

(54) GASTROINTESTINAL RELEASE CAPSULE FOR USE IN A METHOD FOR DESENSITISING AND/OR INDUCING TOLERANCE IN A PATIENT WITH A PEANUT ALLERGY

(71) Applicants: CENTRE HOSPITALIER ET UNIVERSITAIRE DE CLERMONT-FERRAND, Clermont-Ferrand (FR); UNIVERSITE CLERMONT AUVERGNE, Clermont-Ferrand (FR)

(72) Inventors: Jean-Luc Fauquert, Beaumont (FR); Bertrand Evrard, Ceyrat (FR); Elodie Michaud, Charbonnières les varennes (FR); Etienne Merlin, Chamalières (FR)

(73) Assignees: CENTRE HOSPITALIER ET UNIVERSITAIRE DE CLERMONT-FERRAND, Clermont-Ferrand (FR); UNIVERSITE CLERMONT AUVERGNE, Clermont-Ferrand (FR)

( * ) Notice: Subject to any disclaimer, the term of this patent is extended or adjusted under 35 U.S.C. 154(b) by 31 days.

(21) Appl. No.: 16/484,656

(22) PCT Filed: Feb. 9, 2018

(86) PCT No.: PCT/EP2018/053344
§ 371 (c)(1),
(2) Date: Aug. 8, 2019

(87) PCT Pub. No.: WO2018/146274
PCT Pub. Date: Aug. 16, 2018

(65) Prior Publication Data
US 2020/0038466 A1 Feb. 6, 2020

(30) Foreign Application Priority Data

Feb. 10, 2017 (FR) ........................ 1751101

(51) Int. Cl.
| | | |
|---|---|---|
| *A61K 36/48* | (2006.01) | |
| *A61K 47/02* | (2006.01) | |
| *A61K 47/26* | (2006.01) | |
| *A61K 47/44* | (2017.01) | |
| *A61P 37/08* | (2006.01) | |

(52) U.S. Cl.
CPC .............. *A61K 36/48* (2013.01); *A61K 47/02* (2013.01); *A61K 47/26* (2013.01); *A61K 47/44* (2013.01); *A61P 37/08* (2018.01)

(58) Field of Classification Search
CPC ........ A61K 36/48; A61K 47/02; A61K 47/26; A61K 47/44; A61K 45/06; A61K 9/485; A61P 37/08
See application file for complete search history.

(56) References Cited

U.S. PATENT DOCUMENTS

| | | | | |
|---|---|---|---|---|
| 8,691,796 B2 * | 4/2014 | Lin | .......................... | A61P 29/00 514/62 |
| 2014/0271721 A1 | 9/2014 | Walser | | |
| 2015/0328294 A1 * | 11/2015 | O'Hehir | .................. | A61P 37/06 424/185.1 |
| 2016/0243217 A1 * | 8/2016 | Nadeau | ................... | A61P 29/00 |

FOREIGN PATENT DOCUMENTS

WO   2016134291 A2   8/2016

OTHER PUBLICATIONS

International Search Report dated Apr. 20, 2018 for corresponding International Application No. PCT/EP2018/053344, filed Feb. 9, 2018.
Written Opinion of the International Searching Authority dated Apr. 20, 2018 for corresponding International Application No. PCT/EP2018/053344, filed Feb. 9, 2018.
Anonymous: "Oral Desensitization to Peanut in Peanut-Allergic Children and Adults Using Characterized Peanut Allergen OIT", Jun. 23, 2016 (Jun. 23, 2016), XP055411613.
Anonymous: "OIT Gets Ready for Prime Time-Allergic Living", Jul. 18, 2016 (Jul. 18, 2016), XP055411614.
English translation of the Written Opinion of the International Searching Authority dated May 4, 2018 for corresponding International Application No. PCT/EP2018/053344, filed Feb. 9, 2018.
Fauquert JL et al. "Peanut Gastro-Intestinal Delivery Oral Immunotherapy in Adolescents: results of the build-up phase of a randomized, double-blind, placebo-controlled trial (PITA study). Clin Exp Allergy", Jul. 2018;48(7):862-874. doi: 10.1111/cea. 13148. Epub May 29, 2018. PubMed PMID: 29665158.
Prickett et al., "Ara h 1 CD4+ T cell epitope-based peptides: candidates for a peanut allergy therapeutic.", Clin Exp Allergy. Jun. 2013;43(6):684-97. doi: 10.1111/cea.12113.PMID: 23711131.
Prickett et al., "Ara h 2 peptides containing dominant CD4+ T-cell epitopes: candidates for a peanut allergy therapeutic.", J Allergy Clin Immunol. Mar. 2011;127(3):608-15, e1-5. doi: 10.1016/j.jaci. 2016.09.027. Epub Nov. 18, 2010. PMID: 21093025.
Jones SM, Pons L, Roberts JL, Scurlock AM, Perry TT, Kulis M, Shreffler WG, Steele P, Henry KA, Adair M, Francis JM, Durham S, Vickery BP, Zhong X, Burks AW. Clinical efficacy and immune regulation with peanut oral immunotherapy. J Allergy Clin Immunol. Aug. 2009;124(2):292-300, 300.e1-97, doi: 10.1016/j.jaci.2009.05. 022. Epub Jul. 3, 2009. PMID: 19577283.

(Continued)

*Primary Examiner* — Mina Haghighatian
(74) *Attorney, Agent, or Firm* — David D. Brush; Westman, Champlin & Koehler, P.A.

(57) ABSTRACT

Gastro-intestinal release capsule intended for oral use in a method for desensitizing and/or inducing tolerance in a peanut-allergic subject or, alternatively, for diagnosing a peanut allergy in a subject. The capsule has a shell and a core, the core has a composition of peanut including peanut, at least one oil, at least one first pulverulent excipient and, optionally, at least one second prebiotic excipient. The capsule is provided and ingested in an unopened form.

26 Claims, 3 Drawing Sheets

(56) References Cited

OTHER PUBLICATIONS

Wasserman R.L., Sugerman R.W., Mireku-Akomeah N., Gallucci A.R., Pence D.M.,Long N.A. Peanut Oral Immunotherapy (OIT) of Food Allergy (FA) Carries a Significant Risk of Eosinophilic Esophagitis (EoE), J Allergy Ciin Immunol. Feb. 2011;127(2). Supl AB28. DOI:https://doi.org/10.1016/j.jaci.2010.12.121.

Dirks CG, Pedersen MH, Platzer MH, Bindslev-Jensen C, Skov PS, Poulsen LK. Does absorption across the buccal mucosa explain early onset of food-induced allergic systemic reactions? J Allergy Clin Immunol. Jun. 2005;115(6):1321-3. doi: 10.1016/j.jaci.2005.03.027. PMID: 15940158.

Wensing M, Penninks AH, Hefie SL, Koppelman SJ, Bruijnzeel-Koomen CA, Knulst AC. The distribution of individual threshold doses eliciting allergic reactions in a population with peanut allergy. J Allergy Clin Immunol. Dec. 2002;110(6):915-20. doi: 10.1067/mai.2002.129235. PMID: 12464959 Clinical Trial.

\* cited by examiner

GASTROINTESTINAL RELEASE CAPSULE FOR USE IN A METHOD FOR DESENSITISING AND/OR INDUCING TOLERANCE IN A PATIENT WITH A PEANUT ALLERGY

1. CROSS-REFERENCE TO RELATED APPLICATIONS

This application is a Section 371 National Stage Application of International Application No. PCT/EP2018/053344, filed Feb. 9, 2018, the content of which is incorporated herein by reference in its entirety, and published as WO 2018/146274 on Aug. 16, 2018, not in English.

2. FIELD OF THE INVENTION

The field of the invention is that of pharmaceutical compositions and medical indications. More specifically, the invention relates to a gastrointestinal release capsule comprising a core and a shell, said core comprising a peanut composition. Said capsule is intended for use by ingestion for gastrointestinal release enabling a method of oral immunotherapy by gastrointestinal release to desensitize peanut-allergic subject and/or induce tolerance to peanuts in this peanut-allergic subject. Said capsule is also intended for diagnosing peanut allergy in a subject suspected to have peanut allergy.

3. PRIOR ART

Peanut allergy affects 1% to 2% of the child population. It is the primary food allergy among children above the age of three. Unlike allergy to poultry eggs or cow's milk, peanut allergy disappears in only 20% of cases (Rancé et al, *Clin. Exp. Allergy,* 2005, 35:167-172). It is potentially serious: the ingestion of small quantities of peanut can in fact lead to serious or even life-threatening reactions. These reactions follow an immunoglobulin E (IgE) type mediated mechanism in terms of both the original reaction (which leads to the diagnosis of peanut allergy) and subsequent unforeseeable reactions during accidental or masked ingestion.

These allergic reactions, which arise after ingestion of the allergen, include respiratory manifestations (spasmodic coughing, dyspnea, asthma attacks), cutaneous manifestations (urticaria, chemosis, angioedema affecting the skin and/or the mucosae of the upper respiratory tracts, causing laryngeal dyspnea) digestive manifestations, abdominal pains, nausea, vomiting, diarrhea) or general manifestations ranging from simple discomfortto acute anaphylaxis with or without cardiovascular collapse inducing shock. These severe symptoms are especially related to the peanut allergen fraction Ara h2, as well as to other peanut storage allergens such as Ara h1, Ara h3 and Ara h6. The manifestations can also relate to disorders of the upper respiratory tracts (rhinitis, conjunctivitis or oral allergy syndrome, erythema or oedema affecting the buccal mucosa or even the pharynx) or of the upper digestive tracts including eosinophilic oesophagitis. Peanut aversion is also part of the classic signs of the disorder. These signs are often associated and different stages of seriousness have been described in the literature (Lieberman P, Nicklas R A, Oppenheimer J et al, The diagnosis and management of anaphylaxis: an updated practice parameter. J. Allergy Clin. Immunol. 2010; 126: 477-80). Peanut-allergic children are therefore constantly exposed to anaphylactic risk which is regularly reported and discussed in the medical literature (EAACI Guidelines on allergen immunotherapy: IgE-mediated food allergy. Allergy. 2017 Sep. 27. doi: 10.1111/a11.13319).

The diagnosis of peanut allergy is based on the presence of a clinical history evoking post-ingestion reaction in a patient sensitized by prior contact with peanuts. A positive cutaneous test and peanutserum-specific IgE dosage demonstrates the patient's sensitivity to peanuts. In the event of doubt as to the responsibility of peanuts, a food challenge (FC) exercise must be performed to demonstrate the relationship between the allergen and the reaction that it causes. Thus, FC is considered to be the "gold standard" for establishing certitude of diagnosis of peanut allergy, especially if it is done in a double-blind placebo controlled (DBPC) context. It is also used to determine the peanut reactogenic threshold and thus makes it possible to adapt avoidance measures. Its practice implies particular prevention steps. It must be carried out in a unit that is habituated in performing these steps (precise protocol, anticipated therapy measures) and must be capable of coping with a hyper-acute reactions (there must be an intensive care or resuscitation unit in proximity).

To mitigate the nocebo effect, recourse to the double-blind technique (applied to both patient and physician) is recommended. The specific taste and smell of peanuts in its native form however make this practice difficult, especially if we consider the practice of mixing the peanut composition into the alimentary bolus or food bolus. To be precise, the nocebo effect is the negative counterpart of the placebo effect. It is psychological in nature. More specifically, it appears when the patient develops harmful side effects even when consuming an inert substance. The development of these harmful side effects arises from the fact that the patient is convinced that the substance presented to him is harmful or that it will have harmful effects on him. In the case of peanuts, patients would be quick to develop allergies if they think that they are allergic to peanuts or at least would have an allergic reaction triggered at lower thresholds.

Until recent years, the therapeutic treatment of peanut allergy has been limited to the strict avoidance of peanut as a food. The observation that patients who follow strict avoidance have a higher frequency of serious reactions after accidental ingestion of peanuts than children who follow a relative degree of avoidance has led in recent years to the practice of protocols to induce peanut toleranceprotocols without any conclusive results until now. Studies have been set up to test concepts of desensitization or even peanut tolerance using different techniques without any consensus hitherto within the medical community.

The methods of immunotherapy are aimed at reducing the risks of severe or even life-threatening reaction after accidental ingestion of peanuts and at improving the quality of life of patients affected by this ailment. The most widespread methods consist in administering peanut orally. These methods comprise a phase of build-up of the ingesta aimed at desensitizing the patient to the allergen (which requires that the patient should continue to ingest small quantities of allergen in order to be protected), and then a phase of tolerance which protects the patient even when he is no longer ingesting the allergen on a daily basis. As reported in numerous scientific publications, these procedures for orally inducing tolerance are conventionally carried out by mixing the peanut composition or an equivalent into the alimentary bolus. If the peanut composition is formulated in the form of a capsule, this capsule is then ingested in opened form to enable the mixing of the peanut composition into the alimentary bolus. By this means, the medical community recommended an approach based on physio-pathological elements. Indeed, it is commonly recognized that it is preferable or even indispensable to expose the immune cells of the buccal cavity and of the oesophagus to the peanut composition.

In the current state of the literature, immunotherapy is not fully validated as a technique for treating peanut allergy, for reasons related to the acceptability of the treatment and the compliance of the patients and above all to the side effects of these techniques of oral immunotherapy, especially side effects and/or adverse events or effects, including oropharyngeal and digestive manifestations, among them eosinophilic oesophagitis and anaphylactic reactions.

Alternative methods based on other means of allergen penetration, especially sub-lingual or epicutaneous methods have recently been developed. For methods based on epicutaneous application in the form of patches, the transdermal penetration of peanut allergen is lower than that with immunotherapy by oral means and can vary according to the functional quality of the skin (filaggrin deficiency revealed among atopic subjects, age, sex, race, etc.). After accidental ingestion, the doses that penetrate the organism are often high. It must be noted however that no conclusive results have been obtained up to now.

There is therefore a need to propose a simple, efficient and secure means for desensitizing patients to peanuts.

4. SUMMARY OF THE INVENTION

An aspect of the present disclosure relates to a gastro-intestinal release capsule ingested orally, intended for use to desensitize a peanut-allergic subject and/or to induce peanut tolerance in a subject allergic to this allergen, said capsule comprising a shell and a core, said core comprising a composition comprising peanut, at least one oil, at least one first powdery or pulverulent excipient and, optionally, at least one second prebiotic excipient. To this end, said capsule is provided and ingested in anunopened form. In other words, the present invention relates an orally ingested gastro-intestinal release capsule in unopened form (an unopened gastro-intestinal release capsule) intended for use to desensitize a peanut-allergic subject and/or to induce a peanut tolerance in a subject allergic to this allergen, said capsule comprising a shell and a core, said core comprising a composition comprising peanut, at least one oil, at least one first pulverulent excipient and, optionally, at least one second prebiotic excipient.

The term "capsule" is understood to mean a galenic form such as a capsule or gelule with a hard or soft shell, containing a fixed quantity of peanut composition as well as a fixed quantity of excipientsin its core. The peanut composition is therefore isolated within the capsule and is made available only after the capsule is opened and/or after the core is broken. The capsules according to the invention are therefore distinct from forms ingested alone or within the alimentary bolus in the form of non-encased pills, powders and liquid suspensions in that the active principle (namely the peanut in the present case) is not immediately available. The capsules according to the invention are also distinct from capsules ingested in opened form in that the active principle (namely the peanut in the present case) is not immediately available, i.e. in that the active principle does not come into contact with the buccal mucosae.

The term "gastro-intestinal release" is understood to refer to a capsule wherein the opening of the capsule and/or the breaking of the shell occurs in the stomach and/or the small intestine. In other words, the integrity of the capsule is preserved during the ingestion by the mouth and its passage through the oesophagus. The opening of the capsule and/or the breaking of the shell occurs under mechanical and physiological action by the stomach and/or the small intestine. To this end, the capsule according to the present invention is ingested in anunopened form.

The mass percentage is computed by the following formula: mass percentage of a compound A (%)=(mass of A/total mass of the composition)×100.

Thus, the invention relies on a wholly novel and original approach for the oral administration of peanut while masking the characteristic odor, color and taste of peanut and minimizing the risks of allergic reaction in the upper digestive tract and of anaphylactic shock.

In particular, the capsule according to the invention is intended for use in a method for desensitizing and/or making an allergic subject tolerant (inducing tolerance in him) while preventing contact with the buccal, pharyngeal and/or oesophageal mucosae, which are rich in immune cells and in antigen-presenting cells in particular.

Antigen-presenting cells are immune system cellsthat have antigen fragments of the foreign molecule or organism, in this case the allergen, on their cell surface. These cells can be monocytes, macrophages, B lymphocytes or dendritic cells. Schematically, this antigen presentation by immune cells enables a specific activation of the T lymphocytes which will recognize the epitope of the foreign molecule or organism so as to be capable of then eliminating it.

The inventors therefore propose to shunt the buccal cavity, the pharynx and the oesophagus and their reactive immune system to prevent the occurrence of allergic reactions in patients at each desensitization attempt, which would put an end to the therapeutic approach. Indeed, peanut-allergic patients trigger varyingly violent reactions in the event of being put into contact. The unpredictability of these reactions and their intensity means that special precautions must be taken during a peanut immunotherapy protocol. The doses ingested are very small at the beginning of the protocol and increase slowly for a lengthy period to prevent the risk of side effects. In addition, the occurrence of repeated or severe allergic reaction implies stopping the desensitizing protocol. Preventing an excessively violent allergic reaction is therefore crucial to the continuance and success of the method of diagnosis of an allergy and/or peanut desensitization. In addition to these acute reactions to ingestion, the shunt described here above will reduce the risk of the occurrence of chronic manifestations of allergy, especially at the local level of eosinophilic oesophagitis, it must be noted that this approach goes against numerous currently used approaches in which the peanut composition is mixed into the alimentary bolus.

The risks of the subject's non-compliance with the protocol and of its premature interruption are all the greater as this phase is prolonged. Now, the ingestion of the capsule in closed form reduces the risks of non-compliance and of interruption of the protocol. The reduction of side effects and/or adverse events and the masking of the taste thus contribute to high compliance with the protocol on the part of the subject.

In addition, the ingestion of the capsule in closed form limits exposure of the allergens to gastric acid, thus preserving the integrity of their three-dimensional character.

Besides, the mucosa of the small intestine is endowed with numerous cells presenting specialized antigens, especially macrophage or dendritic cell typemononuclear phagocytes. The intestinal dendritic cells thus constitute a set of heterogeneous subpopulations differentially expressing a certain number of phenotype markers, among them CD103, CD11b, CD172a/SIRPα and CX3CR1. These subpopulations have different functional characteristics, some of them in particular being fundamental in establishing oral tolerance to food antigens. These are especially the migratory dendritic cells CD103$^+$CD11b$^-$ and to a lesser extent CD103$^+$CD11b$^+$. Indeed, in a condition of homeostasis, after migration into the mesenteric lymph nodes, these cells are said to have the capacity to produce retinoic acid mediated by an enzyme, RALDH2 (retinaldehyde dehydrogenase 2), as well as TGF-β and to express IDO (indoleamine 2,3-dioxygenase). All these elements enable the conversion of naïve lymphocyte T cells into CD4$^+$CD25$^+$FoxP3 peripheral regulatory T cells CD4$^+$CD25$^+$FoxP3 and enable their homing into the intestinal mucosae. These lymphocytes are then said to be themselves implicated in the inhibition of the food-antigen-specific Th2 and IgE responses, and in the promotion of the IgG4 responses. The dendritic cells could also promote the functioning of other T regulatory lymphocytes, for example of Th3 type, as well as the functioning of the ILCs (innate lymphoid cells) or regulatory B lymphocytes. A disturbance in the functioning of the dendritic cells could thus upset the delicate balance between immunity and tolerance, giving rise to the appearance of a Th2 type response and over-sensitivity to food allergens. The capsule according to the invention enables peanut to be released in the small intestine and places these intestinal dendritic cells in contact with the antigen contained in the peanut composition. Thus, by targeting these intestinal dendritic cells (without intervention by the presenting cells of the oropharynx), our "gastro-intestinal release" immunotherapy acts directly on the cells truly providing in vivo support to the inducing of oral tolerance and optimizing our immunotherapy protocol. It must be noted that the contact between the intestinal dendritic cells and the allergens could take place according to three preferred means, 1) by direct contact through the emission of cytoplasmic extensions by the CX3CR1+ and CD11b+ dendritic cells of theLamina propriapassing between the epithelial cells and capturing the food allergens directly in the intestinal lumen; 2) by indirect contact following the transcytosis of the allergens through M cells situated above the Peyer patches; 3) by indirect contact via the intestinal epithelial cells capable of internalizing the allergens at their apical pole, then secreting a cytokine tolerogenic environment at their basal pole in contact with the dendritic cells, as well as the allergen-peptide-bearing exosomes.

The stimulation of the antigen-presenting cells in the small intestine is therefore a promising way to stimulate the patient's immune system in limiting the risks of allergic reaction. In preventing contact with the buccal, pharyngeal and oesophagal mucosae, the composition according to the invention makes it possible, on the one hand, to achieve desensitization and, on the other hand, to ease the precautions taken during tests of desensitization or ingestion in the treatment.

The masking of the characteristic taste, color and odor of peanuts furthermore considerably reduces or even eliminates the nocebo effect. Indeed, it can be noted that patients suffering from peanut allergy have a food aversion that is a characteristic symptom of the disease. By consciously and visibly ingesting peanut, the harmful effect of which they are conscious, they are liable to develop symptoms that are in every way identical to those of an allergic reaction. According to the invention, the capsule enables the utmost compliance with the principle of the double blind test.

If necessary, as is now illustrated, the peanut can be processed beforehand. For example, the peanut can be processed in the form of a paste, for example by the addition of oil. Peanut paste thus constitutes the raw material of the peanut composition.

The presence of a first pulverulent excipient is useful in that it makes it possible to obtain a peanut composition in the form of powder independently of the raw material used, such as peanut paste. This form facilitates the preparation and processing of the peanut composition.

The presence of a second prebiotic excipient boosts the commensal flora and contributes to boosting the immunity of the treated subject.

The formulation of the peanut composition with these first and second excipients also modifies the absorption of the peanut by the intestinal mucosa.

The capsule thus optimized maintains a presentation of the allergen in intact form and responds to the goal of a peanut immunotherapy.

The capsule according to the invention preferably comprises a composition of roasted peanuts, very preferably a composition of roasted, full-fat peanuts.

The capsule according to the invention preferably comprises 10 mg to 1000 mg, very preferably 10 mg to 75 mg, and again very preferably 10 mg to 500 mg of peanut.

Said composition according to the invention can include 5% to 70% of peanut relative to the total weight of the composition. In addition, said composition can include 15% to 55% of first pulverulent excipient relative to the total weight of the composition. Similarly, said composition can include 10% to 75% of the second prebiotic excipient, if any, relative to the total weight of the composition.

The capsule can have different sizes. The size of the capsule can be suited to its mass while, at the same time, complying with the notion of the pharmaceutical blind. Thus, with regard to the active principles, excipients and other compounds, their respective proportions will be adjusted in such a way that the appropriate dose of active principles is ingested by the subject to be treated depending on the step in progress.

Advantageously, the peanut composition comprises 10% to 40%, preferably between 10% to 30%, and very preferably 15% to 25% of allergen proteins relative to the total weight of said composition. Indeed, the inventors have highlighted the fact that, in order to avoid allergic reactions during the immunotherapy protocol and in order to obtain effective desensitization, it is preferable to use peanuts having a limited proportion of allergenic proteins, i.e. a proportion below 40%, instead of peanuts having a high proportion of allergenic proteins.

As a corollary, said peanut composition comprises 10% to 15% of the total proteins for the allergen fraction Ara h1, 2% to 10% of the total proteins for the allergen fraction Ara h2 and 10% to 20% of the total proteins for the allergen fraction Ara h3; preferably about 12% of the total proteins for the allergenfraction Ara h1, about 6% of the total proteins for the allergen fraction Ara h2, and about 15% of the total proteins for the allergen fraction Ara h3, by weight of the protein fraction of said composition. This particular composition in allergens, present in limited proportions, makes it possible to combine the most frequent allergen fractions among the wide diversity of peanut varieties. Thus, the capsule according to the invention is exhaustive and universal for desensitization to peanut allergies. It is indeed promising that a patient/subject should be capable of being desensitized at different allergen fractions simultaneously, so that he can resume normal life without any worry about the variety of peanut used in a dish or the variety of peanut that has potentially contaminated a food product.

Said capsule preferably includes an oil that is sunflower oil. Allergy to sunflower oil is exceptional and does not expose subjects to risks of severe reactions. The fact is that it is not rare for peanut-allergic patients to have other food sensitivities or allergies, especially to walnut oil, hazelnut oil or colza. Said composition can comprise 0.5% to 5% by weight of said oil relative to the total weight of said composition.

Said capsule comprises a first pulverulent excipient that can be tricalciium phosphate, very preferably a first pulverulent excipient chosen from among beta tricalcium phosphate, alpha tricalcium phosphate and their mixture; as an alternative, beta tricalcium phosphate or alpha tricalcium phosphate. The formulation of the peanut composition with the tricalcium phosphate is more advantageous than other pulverulent excipients. Indeed, tricalcium phosphate is a potential additive of immunity. In particular, tricalcium phosphate possesses promising immune-modulator properties, unlike other forms of phosphate. This function contributes therefore to the desensitization of the subject being treated.

Said capsule can furthermore comprise a second prebiotic excipient. Said second prebiotic excipient is preferably lactose, very preferably lactose monohydrate. The formulation of the peanut composition with a second prebiotic excipient, especially lactose, is advantageous in that said second prebiotic excipient contributes to improving the quality of the digestive commensal flora which is essential in that it largely contributes to the "education" of the immune system and in that it is an essential factor in limiting the occurrence of allergy functions (at the level of the population).

Said capsule according to the invention comprises 20 mg to 315 mg of the first pulverulent excipient and/or 0 mg to 100 mg of the second prebiotic excipient.

The shell of said capsule is preferably opaque. An opaque shell prevents the patient and/or the practitioner from distinguishing the capsule containing the peanut composition from a placebo for example. The shell can comprise a compound chosen from among the group consisting of gelatin (of animal or marine origin), hydroxypropyl methylcellulose (HPMC), pullulan and their mixtures. In this respect, the capsule according to the invention can also include an opacifier and/or coloring agents in its shell in keeping with their inertia at the allergenic level.

The shell of the capsule can include a body and a head, the head being fixed to the body to close the capsule. In particular, the closed capsule can have a length of 5 mm to 30 mm. The head of the capsule can have a length of 5 mm to 15 mm and a diameter of 4.5 mm to 10 mm. The body of the shell can have a length of 5 mm to 25 mm and a diameter of 4.5 mm to 10 mm.

The capsule as defined here above can be used to determine a peanut allergen threshold. This threshold is determined in vivo by the performance of a challenge test. This test warrants special preventivesteps and a practiced team as well as the presence of a nearby intensive-care unit. The occurrence of objective clinical reactions, even in isolation, defines the reactivity threshold (table 4) (Rancé F., Deschildre A, Villard-Truc F, Gomez S A, Paty E, Santos C, Couderc L, Fauquert J L, De Blic J, Bidat E, Dupont C, Eigenmann P, Lack G, Scheinmann P, SFAIC and SP2A workgroup on OFC in children. Oral food challenge in children: an expert review. Position paper of the Section of Pediatrics of the French Society of Allergology and Clinical Immunology (SFAIC) and of the Pediatric Society of Pulmonology and Allergology (SP2A). Eur Ann Allergy Clin Immunol 2009; 41; 2:35-49.).

The diagnosis of peanut allergy must be preferably based on the practice of a double-blind food challenge test (FCT) during which peanut or its allergens are administered to the patient. The characteristic odor and taste of peanut makes it difficult to comply with the double blind principle or carry out diagnosis. Besides, the possibility that a reaction will occur or be intensified by knowledge of the presence of the allergen can never be ruled out. The capsule and its ingestion in enclosed (unopened) form—concealing the appearance, odor, color and flavor of its content—makes it possible to avoid all these drawbacks. In addition, the presence of at least one first pulverulent excipient and, optionally, at least one second excipient improves its intestinal absorption.

The invention more particularly relates to the capsule as defined here above for use in a method for desensitizing and/or obtaining (inducing) tolerance in a peanut-allergic subject. The desensitization approach can also be designated by the expressions "specific immunotherapy" or "allergen vaccinotherapy". The desensitization consists in gradually making the organism habituated to an allergen by administering increasing doses of a composition comprising the allergen until the efficient dose is obtained. The desensitized patient then has far more moderate allergy reactions, or even no longer has any such reactions, in the presence of the allergens in question. In the case of peanut-allergic patients, the desensitization enables them to consume foodstuffs that have been potentially in contact with peanuts, or even peanut-containing foodstuffs.

The subject to be desensitized is preferably 1 to 18 years of age. Children and adolescents are particularly exposed to accidental ingestion of peanut. For example, children or adolescents can be exposed to peanuts when eating in a school cafeteria, sharing sweets with their schoolmates or eating sweets alone because they are unaware of the potential presence of peanuts or traces of peanuts in foodstuffs. The desensitization approach therefore is particularly useful among children and adolescents. Adolescents allergic to peanuts are known to be particularly exposed to anaphylactic risks and the reactions that they show during accidental ingestion are often severe with accentuated life-threatening risks. As an alternative, the subject can be 18 years old or more (more than eighteen years).

Advantageously, the capsule according to the invention is provided and administered orally (ingested) in aunopened and unmixed form into the alimentary bolus. Maintaining the integrity of the capsule during ingestion is essential at present in that it prevents the immune cells present in the mouth cavity, the pharynx and the oesophagus from being put into contact with peanut. Thus, the peanut is put into contact only with the immune cells of the stomach and small intestine. Although many protocols require that the capsule should be opened and/or that the shell should be broken before ingestion in order to mix it into the alimentary bolus, the inventors have demonstrated that shunting the immune system of the buccal cavity, the pharynx and the oesophagus and specifically targeting the immune system of the small intestine give an efficient method of desensitization while minimizing risks of allergy reactions.

The method of immunotherapy according to the invention consists of a phase of induction of a tolerogenic response of the immune system and/or desensitization, followed by a phase of keeping up or maintenance.

The desensitizing phase can consist of the daily administration of at least one capsule of an average peanut dose increasing from 10 mg to 2 g for 28 weeks, preferably for 24 weeks. The average peanut dose is preferably increased by a maximum factor of 2 per stage every 10 to 18 days, preferably every 14 days. The average increasing doses of peanut can be for example: 10 mg/day, 20 mg/day, 40 mg/day, 80 mg/day, 160 mg/day, 300 mg/day, 500 mg/day, 750 mg/day, 1000 mg/day, 1250 mg/day, 1500 mg/day, and 2000 mg/day.

The keeping up phase can consist of the administering of a daily average dose of peanut of the order of 2 g, preferably a daily average dose of peanut of 2 g to 5 g. The maintenance phase is implemented with subjects aged 1 to 18 years, as an alternative subjects aged eighteen years or more, tolerating a cumulated dose of peanut of over 2 g.

In another aspect, the present invention also relates to a gastro-intestinal release capsule as defined here above, intended for oral use in a method enabling the diagnosis of peanut allergy in a subject.

5. LIST OF FIGURES

Other features and advantages of the invention shall appear more clearly from the following description of a preferred embodiment given by way of a simple illustratory and non-exhaustive example, and from the appended figure presenting a block diagram of the progress of the protocol of the clinical study.

6. DESCRIPTION OF ONE EMBODIMENT OF THE INVENTION

Figure 1:
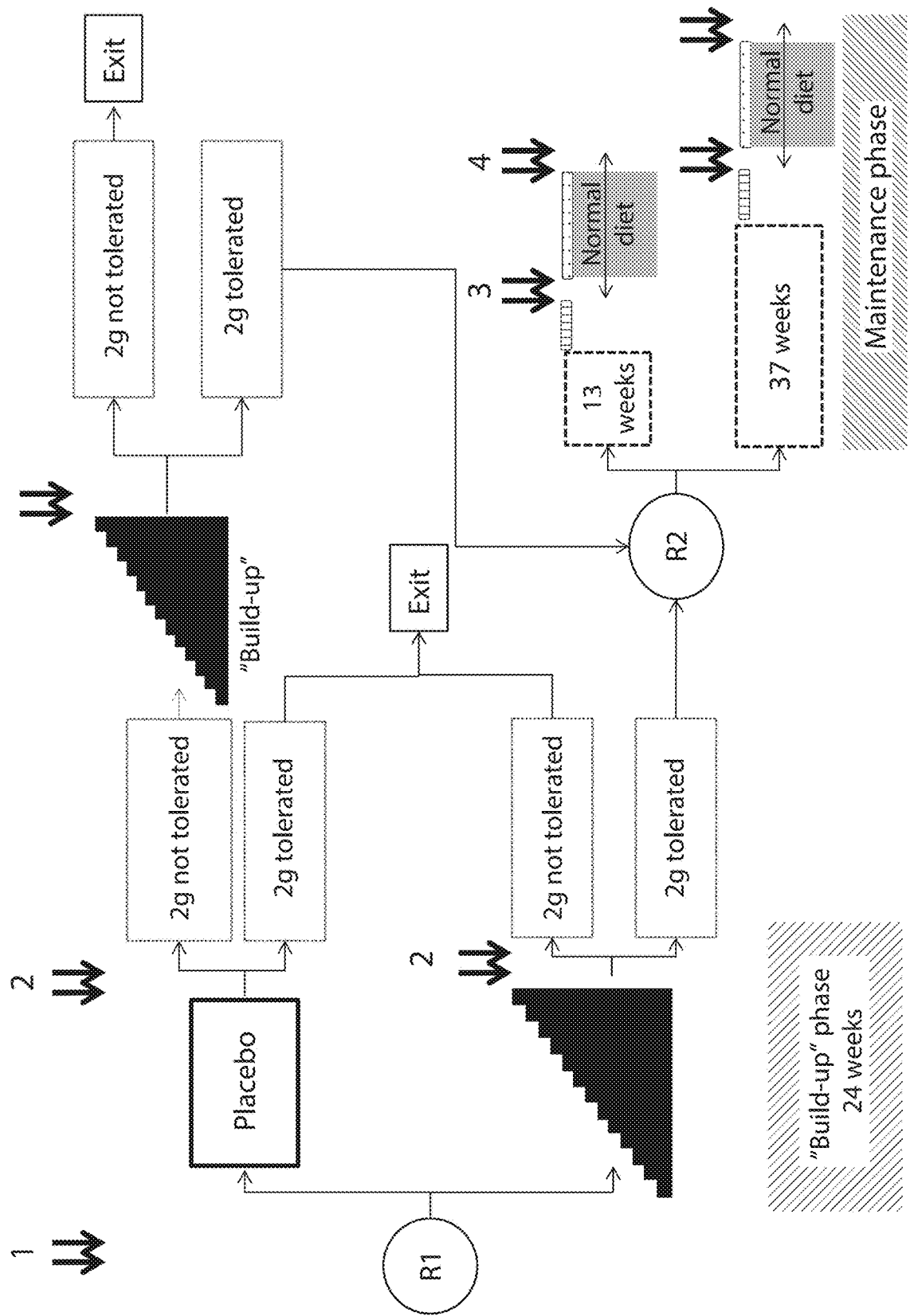
FIG. 1 is a first diagram giving a schematic view of the progress of the study.

The general principle of the invention relies on the formulation of capsules comprising peanut paste and the gastro-intestinal release of peanut (ingestion in unopened form) so as to be used, on the one hand, in the reliable and precise diagnosis of peanut-allergy and of the allergy-activation threshold and, on the other hand, in the desensitization of peanut allergy. The formulation in the form of capsules and their ingestion in closed form therefore prevents or at the very least greatly reduces the nocebo effect that could falsify peanut allergy diagnostic tests. It also makes it possible to obtain precise and simple knowledge of the peanut dose administered to the patient. Finally, it facilitates the desensitization protocol for the patient, especially by preventing any contact with the buccal mucosa which is rich in immune cells.

6.1. Examples of Composition of Capsules According to the Invention

The peanut paste used as a raw material is composed of 95.7% of peanuts, 4.3% of sunflower oil and at least one excipient, namely tricalcium phosphate (a pulverulent excipient) and optionally lactose (prebiotic excipient). Peanut paste is obtained by mixing peanuts with said oil in order to obtain a raw material. This peanut paste is then mixed with excipients in order to obtain a peanut composition according to the invention. Thus, the peanut paste is incorporated in powder form into capsules of different sizes.

The sizes of the capsules correspond to very precise standards. The shell of each capsule is composed of a head and a body, the body being filled with peanut paste before the head encloses the body.

The capsules according to the invention can be of all sizes, from size 000 (the biggest) to size 4 (the smallest).

TABLE 1

Detailed view of standards for capsule sizes

|  | 000 | 00 | 0 | 1 | 2 | 3 | 4 |
|---|---|---|---|---|---|---|---|
| Length of closed capsule (mm) | 26.1 | 23.3 | 21.7 | 19.4 | 18.0 | 15.9 | 14.3 |
| Body length (mm) | 22.2 | 20.2 | 18.4 | 16.6 | 15.3 | 13.6 | 12.2 |
| Head length (mm) | 12.9 | 11.7 | 10.7 | 9.8 | 8.9 | 8.1 | 7.2 |
| Body diameter (mm) | 9.5 | 8.2 | 7.3 | 6.6 | 6.1 | 5.6 | 5.0 |
| Head diameter (mm) | 9.9 | 8.5 | 7.6 | 6.9 | 6.3 | 5.8 | 5.3 |

Source: Technical Reference File, "CAPSUGEL - Gélules Coni-Snap" 1st edition

According to all methods well known to those skilled in the art, different capsules are formulated enclosing peanut paste and an excipient.

TABLE 2

Examples of compositions of capsules according to the invention

| Dosage (mg) | Peanut paste (mg per capsule) | Tricalcium phosphate (mg per capsule) | Lactose (mg per capsule) | Capsule size |
|---|---|---|---|---|
| 10 | 10.43 | 20.86 | 90 | 4 |
| 20 | 20.86 | 41.72 | 50 | 4 |
| 40 | 41.72 | 41.72 | 20 | 3 |
| 80 | 83.44 | 83.44 | 0 | 3 |
| 160 | 166.88 | 166.88 | 0 | 0 |
| 250 | 260.75 | 260.75 | 100 | 00 |
| 300 | 312.9 | 312.9 | 0 | 00 |
| 500 | 521.5 | 180 | 100 | 00 |

The protein content of the peanut paste is quantified on the basis of samples of non-roasted raw peanuts. This enables, on the one hand, the reserve proteins contained in the seed to be made accessible for extraction and, on the other hand, the avoidance of Maillard reactions which adversely affect the dosage. The protein extracts are then quantified by the bicinchoninic acid method (the Pierce method, cf. Smith, P. K. et al., Measurement of protein using bicinchoninic acid. Anal. Biochem. 150 (1985) 76-85). For the *Arachis hypogeae* used, the composition in main allergen fractions of peanut paste has been analyzed and quantified by the Elisa method. This composition amounts respectively to 12%, 15% and 6% for the Ara h 1, Ara h 3 and Ara h 2 content.

TABLE 3

Allergen fraction Ara h1, Ara h2 and Ara h3 content.

| Dosage (mg) | Peanut paste (mg per capsule) | Protein (mg) | Ara h 1 (mg) | Ara h 3 (mg) | Ara h 2 (mg) | Capsule |
|---|---|---|---|---|---|---|
| 10 | 10.43 | 2.2 | 0.26 | 0.33 | 0.13 | 4 |
| 20 | 20.86 | 4.38 | 0.53 | 0.66 | 0.26 | 4 |
| 40 | 41.72 | 8.76 | 1.05 | 1.3 | 0.53 | 3 |
| 80 | 83.44 | 17.52 | 2.1 | 2.63 | 1.05 | 3 |
| 160 | 166.88 | 35.04 | 4.2 | 5.26 | 2.1 | 0 |
| 250 | 260.75 | 54.76 | 6.6 | 8.2 | 3.3 | 00 |
| 300 | 312.9 | 65.71 | 7.9 | 9.86 | 3.9 | 00 |
| 500 | 521.5 | 109.52 | 13.1 | 16.4 | 6.6 | 00 |

6.2. Clinical Trial on an Adolescent Population

The main goal of the study is to evaluate the efficacy of a peanut desensitization protocol by ingestion of increasing doses of peanut up to a maximum of 2 grams per day. Desensitization to peanuts will be defined by the absence of objective clinical symptoms after ingestion of a cumulated dose of 2 g of peanuts during a double blind placebo-controlled (DBPC) food challenge test (FCT) at the end of a phase of induction of the protocol (FCT2).

Choice of the Population Studied

Protocols for the induction of peanut tolerance have taken an interest in very heterogeneous populations of children aged 1 to 18 years. To date, the present applicant is not aware of any clinical study that has included solely adolescents. However, adolescence is a period that is particular risky as regards reaction after accidental ingestion. Indeed, an adolescent is less subject to spontaneous healing than a younger child. Besides, fixed doses of peanuts used in tolerance induction protocols or diagnostic tests (FCT) are more homogenous relative to the body surface area.

The threshold of 500 mg of peanuts determines the state of traces for a quantity of 1000 g of native foodstuff: (ftp://ftp.fao.org/docrep/fao/010/y4705f/y4705f02.pdf). The 2 g dose, namely four times the "trace" threshold, characterizes the acquisition of a tolerance to traces of peanut. Thus, patients who tolerate ingestion of 2 g of peanuts are assumed to be free of risk of reaction to a food diet containing peanut traces.

Description of the Research Methodology

Figure 2:
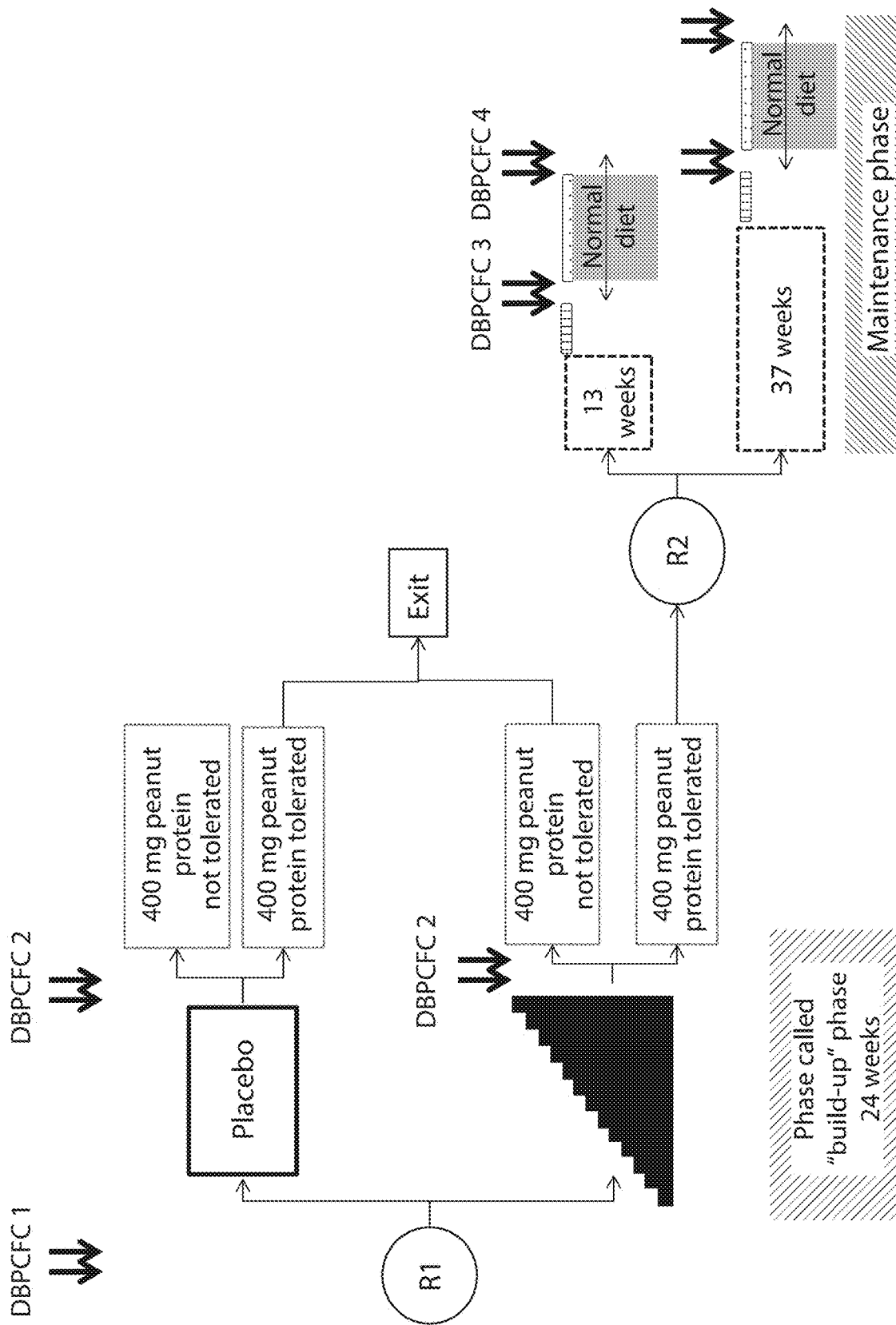
FIG. 2 is a second diagram giving a schematic view of the progress of the study.

The study is multicenter double-blind, randomized, placebo-controlled approach and consists of two phases. FIGS. 1 and 2 are block diagrams of the progress of the protocol and of the methodology used.

The first phase is a phase of desensitization. The patients receive increasing doses, for 24 weeks, of either placebo or the capsule according to the invention. The treatment starts with 10 mg/day until it reaches 2 g/day of peanuts or placebo at the end of 24 weeks. The increase in the dose is done in stages, every 14 days. Depending on the occurrence and intensity of side effects, it is possible to carry out stagnation phases (of 14 days) in the dose inducing side effects.

The stages are the following: 10 mg/day, 20 mg/day, 40 mg/day, 80 mg/day, 160 mg/day, 300 mg/day, 500 mg/day, 750 mg/day, 1000 mg/day, 1250 mg/day, 1500 mg/day et 2000 mg/day.

The use of the capsule according to the invention makes it possible to maintain the double blind. Thus, this method attenuates the psychogenic effects in the patient that could be associated with the ingestion of allergen as well as aversion to native peanuts. Besides, the practitioner who evaluates and grades the side effects remains objective in his assessments. Finally, the immune cells of the buccal cavity are not affected.

The second phase is a phase of keeping up. To be eligible for the keeping-up phase, the patients must tolerate the ingestion of a cumulated dose greater than 2 g of peanuts at the end of the desensitizing phase.

6.2.1. Food Challenge Tests (FCT)

The FCTs consist in ingesting an increasing dose of peanuts every 30 minutes up to 5 grams. In the context of this protocol, all FCTs will be carried out in under DACP and will make it possible to determine the maximum tolerated dose. The reaction during FCT is defined by the occurrence of objective clinical manifestations. The double blind is lifted after the practice of each FCT, thus making it possible to confirm or not confirm the diagnosis of peanut allergy. It is carried out before the desensitization phase (FCT1) and at the end of this period of 24 weeks (FCT2), independently of the tolerance induction protocol with which it bears no relationship whatsoever. The expected undesirable events are those described as being a possible consequence of a food challenge test. They are listed in table 4 here below.

TABLE 4

Adverse events and authorized treatments

| Signs | Subjective signs | Treatment | Objective signs | Treatment |
|---|---|---|---|---|
| Local | | | Conjunctivitis | 2 ± 3 |
| | | | Rhinitis, repeated sneezing, nasal obstruction, watery nasal discharge | 2 ± 3 |
| | Isolated pruritus of the lips, soft palate and pharynx | 0 or 3 | Oral allergy syndrome: soft palate prurutis, œdema of the lips and dysphagia | 0 ou 3 |
| | Dysphagia | 0 or 3 | Enanthema | 3 |
| | | | Oedema of the uvula | 3 ± 5 |
| Cutaneous | | | Pruritus | |
| | Isolated | 0 or 3 | Generalized or palmo-plantar | 3 |
| | | | Erythema | 0 or 3 |
| | | | Macular-papular rash | |
| | | | Urticaria | 3 |
| | | | Angio-oedema | 3 ± 5 |
| | | | Eczema | 1 ± 3 |
| Digestive | | | Abdominal pains | |
| | Isolated | 0 or 1 | Repeated or associated | 2 0 or 3 |
| | Nausea | 0 or 1 | Vomiting | |
| | | | Diarrhea | |
| Respiratory | | | Voice alteration | 3 |
| | | | Laryngeal dyspnea, stridor | 3 ± 5 |
| | | | Coughs, wheezing, dyspnea, acute asthma | 4 ± 5 |
| | | | Reduction of FEV>15% | |
| | | | Lowering of PF>20% | |
| General | Tiredness | 0 or 1 | Abnormal pallor | 0 |
| | Behavioral problems | 0 | Acceleration of pulse >20% | 0 or 5 |
| | Headaches | 0 or 1 | Lowering of BP>20 mmHg | |

TABLE 4-continued

Adverse events and authorized treatments

| Signs | Subjective signs | Treatment | Objective signs | Treatment |
|---|---|---|---|---|
| | Apprehension, refusal to take the next dose | 0 or 1 | Lowering of SaO2 | 4 ± 5 |
| | | | Discomfort Anaphylactic shock | 5 ± 6 |

The authorized treatments are classified as follows:

0. Therapeutic abstention
1. Treatment of symptoms: emollients or dermocorticoids, anti-emetics, anti-spasmodics, paracetamol
2. Antihistamines by local treatment
3. Antihistamines by general treatment
4. Beta 2 mimetics inhaled.
5. Systemic glucocorticosteroids
6. Adrenalin Anaphylaxis is defined as the rapid appearance (within a few minutes to a few hours), after exposure to a probable allergen, of symptoms indicating that two organs are affected (Sampson et al. *J. All. Clin. Immunol.*, February 2006; 117(2):391-397). For example, the dermatological symptoms in question are pruritus or generalized rash, oedema of the lips, the tongue or the uvula. Respiratory symptoms are dyspnea, wheezing, laryngeal cough, the reduction of the peak flow and hypoxemia. The digestive symptoms are stomach cramps, vomiting and diarrhea. The general symptoms are a drop in blood pressure or the association of organ failure symptoms: hypotonia, fainting, incontinence, etc.

These symptoms are classified by stage of seriousness according to the modified Ring and Messmer classification (*The diagnosis and management of anaphylaxis: an updated practice parameter*. J. Allergy Clin. Immunol. 2005; 115: S483-523):

Grade 1: conjunctivitis, rhinitis, oral allergy syndrome, simple generalized urticaria, oedema of the lips and/or of the face without symptoms of asphyxia (respiratory discomfort), coughs or isolated wheezing, nausea or stomach pains;

Grade 2: moderate multi-organdys function with cutaneous-mucosal signs (angioedema)±digestive signs (vomiting, diarrhea)±asthma (acute bronchial spasm): coughing, dyspnea, wheezing, drop in peak flow (15% or more of the expected or known values)±tiredness and tachycardia;

Grade 3: life-threatening severe multiple-organ failure requiring specific therapy: bronchial spasms or signs of laryngeal oedema with signs of asphyxia, anaphylaxis (symptoms of failure in several organs, including respiratory symptoms) and anaphylactic shock (discomfort, agitation, fainting, collapse), cardiovascular collapse, tachycardia or bradycardia, cardiac rhythm disorders; et Grade 4: cardio-respiratory arrest.

Statistical analysis is carried out under STATA12 (Stata-Corp, College Station, Tex.) and R (http://cran.r-project.org/).

6.2.2. Results

Among the 53 patients tested, 30 patients have been included because they showed an allergy development threshold of 100 mg to 2000 mg of peanut. At the beginning of the study, no significant statistical difference appears between the test group and the control group in terms of age, sex, body mass index, measurement of total and specific IgE dosages, typeof reaction observed in diagnosis or number of occurrences of severe reactions after diagnosis, respiratory pathologies or pathologies associated with food intake or even in terms of medical history.

Clinical Efficacy

The clinical efficacy results are presented in table 5. Among the 30 patients included, 28 patients followed the second phase of the food challenge test, 19 of them were exposed to peanut and 9 to the placebo. 17 of the 21 patients of the peanut group reached the tolerance threshold ofa cumulated value of 2 g of peanut. This threshold was achieved for only 1 out of 9 patients with the placebo ($p<0.001$). A significant increase was observed in the threshold of positivity during the FC test among patients of the treated group ($p<0.001$). This threshold increased 15 times in the treated group and 3 times in the placebo group. In addition, the number of patients whose tolerance threshold quadrupled between the first FC test and the second FC test was also significantly greater among patients in the peanut group than among patients in the placebo group ($p<0.001$).

TABLE 5

Clinical efficacy

| | | Peanut (n = 19) | Placebo (n = 9) | p |
|---|---|---|---|---|
| FC test 2 at 2 grams | Negative* | 17 (89%) | 1 (11%) | <0.001 |
| | Positive** | 2 (11%) | 8 (89%) | |
| Reactivity threshold | FCT1 m; [Q25 Q75] | 610 [610-2000] | 610 [310-1100] | 0.38 |
| | FCT2 m; [Q25 Q75] | 9000 [4000-9000] | 2000 [1100-2000] | <0.001 |
| | p (TPO2/TPO1) | p < 0.001 | p = 0.02 | |
| | X4 | 17 | 2 | <0.001 |

Legend:
*= patients not tolerating a cumulated value of 2 g of peanut
**= patients tolerating a cumulated value of 2 g of peanut
m = average
Q25 = $1^{st}$ quartile
Q75 = $3^{rd}$ quartile Tolerance to Treatment The results for tolerance are compiled in table 6. As can be seen, 2 patients were not able to terminate the first phase of induction. The first patient had to leave the study because of moderate adverse events which obliged him to recommence a 14-day stage more than three times, with the same dose of peanut. The second patient suffered anaphylactic shock two hours after taking the peanut capsule, and had to be given epinephrine and emergency treatment. Subsequently, the patient admitted that he had taken twice the prescribed dose of peanut. No reactions or serious side effects were observed in the control group.

Moderate adverse events were observed among the same number of patients: 19/21 patients in the peanut group against 8/9 patients in the control group. However, patients belonging to the peanut group had more adverse events than those in the control group: 6.19+/−3.17 reactions for the peanut group vs. 3.66+/−2.29 reactions for the control group (p<0.05).

Similarly, the number of patients who terminated a 14-day stage without showing adverse events was significantly greater in the control group than in the peanut group (p=0.001). In addition, significant differences were also observed in the intensity of adverse events according to the Ring and Messmer classification. Patients in the control group developed more grade 1 adverse events while patients in the peanut group had more adverse events under grades 2 and 3 (p<0.05).

As regards recourse to emergency treatment, there was no significant difference observed between the two groups. Patients in the peanut group suffered digestive problems (p<0.01) and respiratory problems (p=0.01) in significantly greater numbers than did patients in the control group (68 v. 7, and 61 v. 7 respectively). Adverse oropharyngeal events and dysphagia were rare and were not more frequent in the treated group than in the placebo group (table 6b). No eosinophilic oesophagitis was suspected in the treated group and no patient was excluded because of gastrointestinal symptoms. The general reactions were equally distributed between the placebo group and the treated group. Multiple-organ reactions were rare in the treated group (only one classified as a severe adverse event (SAE) among 19 patients of the patient group) and occurred a minimum of 40 minutes after ingestion of the capsule.

TABLE 6a

Side effects of the peanut tolerance induction phase

|  |  | Peanut group | Placebo group | p |
|---|---|---|---|---|
| N = |  | 21 | 9 |  |
| Severe adverse event (S.A.E.) |  | 1 | 0 | n.s. |
| Exclusion from the protocol |  | 2 | 0 | n.s. |
| Number of patients with A.E | None | 2 | 1 | n.s. |
|  | ≥1 | 19 | 8 |  |
| Number of reactions/patient |  | 6.19 ± 3.17 | 3.66 ± 2.29 | <0.05 |
| Number of two-week stages | Without A.E. | 162/292 | 88/121 | 0.001 |
|  | With A.E. | 130/292 | 33/121 |  |
| Intensity of A.E.* (n=) | 1 | 93 | 30 | <0.05 |
|  | 2 | 32 | 2 |  |
|  | 3 | 5 | 0 |  |
|  | 4 | 0 | 0 | n.s. |

TABLE 6a-continued

Side effects of the peanut tolerance induction phase

|  |  | Peanut group | Placebo group | p |
|---|---|---|---|---|
| Number of A.E | Local | 30 | 8 | n.s. |
|  | Cutaneous | 48 | 16 | n.s. |
|  | Digestive | 68 | 7 | <0.01 |
|  | Respiratory | 61 | 7 | 0.01 |
|  | General | 18 | 2 | n.s. |
| Treatment of A.E. | Yes | 88 | 21 | n.s |
|  | Non | 42 | 12 |  |
| Hospital treatment for A.E |  | 1 | 0 | n.s |

TABLE 6b

Local adverse events (A.E.) during the build-up phase: number of local reactions in brackets: % of patients

| Local A.E. | Peanut (n = 21) | Placebo (n = 9) | p = |
|---|---|---|---|
| Conjunctivitis | 10 (24) | 2 (22) | 0.96 |
| Rhinitis | 21 (43) | 5 (33) | 0.77 |
| Oropharyngeal symptoms | 6 (19) | 1 (11) | 0.71 |
| Dysphagia | 0 (0) | 0 (0) | ns |

Desensitization and Immunological Modifications (Table 7)

The results of the desensitization show that the patients of the group treated with the capsule according to the invention (group Ara) significantly modify their immune balance relative to peanut unlike patients treated with the placebo (group Plac). The cutaneous dermatological tests reveal a reduction in the diameter of the allergic reaction from 12.45±6.71 mm to 6.05±4.06 mm (p<0.0001) between the two FCT phases. Less significant changes were observed in the control group (12.5±6.7 mm to 8±3.7 mm; p<0.05).

Figure 3:
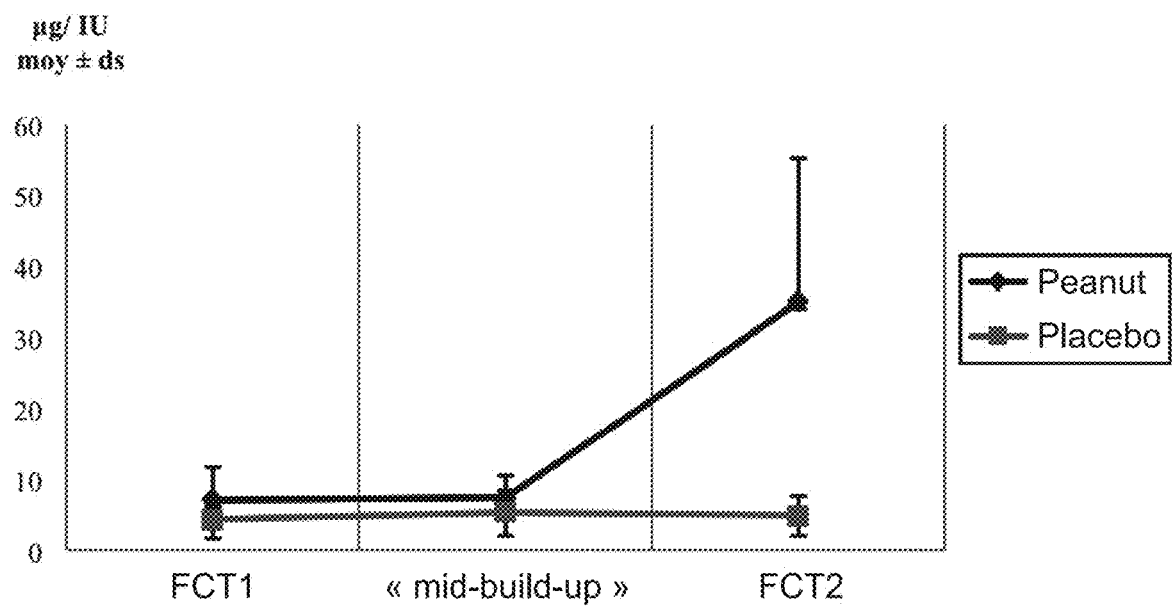
FIGS. 3 and 4 represent the development of the IgG/IgE ratios during the build-up phase.
Figure 4:
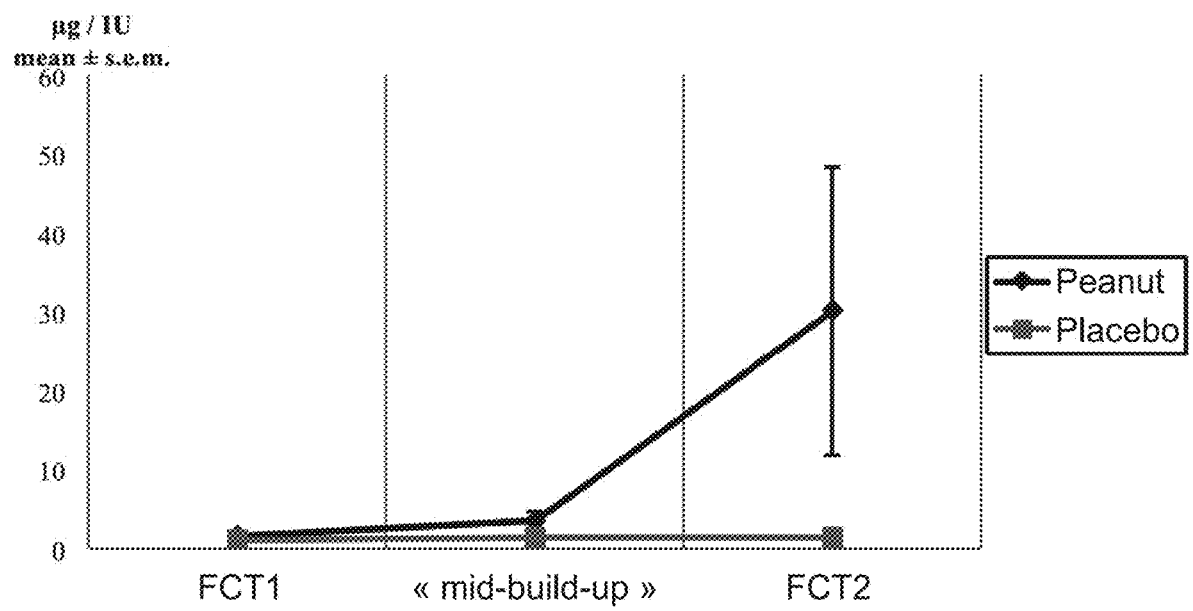

In the peanut group (Ara), the level of peanut serum specific IgE dosages increased significantly throughout this phase of tolerance induction (peanut=0.0001). The same kinetics were observed with specific IgE values of the allergen fraction Ara h2. Significant modifications in reactivity to the allergens Ara h1 and Ara h2 were observed among patients of the peanut group (p=0.01). In particular, the specific IgE dosages of Ara h1 attained significant levels only during the second phase. By contrast, the specific IgE dosages for Ara h3, Ara h8 and Ara h9 did not change significantly among patients of the peanut group as compared with their initial level, and were not at all modified among patients of the control group. Among patients of the placebo group (Plac), no significant modification was observed for specific IgE values of peanut as well as for the different allergen fractions. On the contrary, the specific IgG4 values of peanut increased significantly in the treated group but not in the placebo group. This same was the case for the three main protein fractions Ara h1, Ara h2 andAra h3. The ratio between the specific IgG4/IgE antibodies increased significantly between the start and the end of the build-up phase in the peanut group but remained stable in the control group. The increase in this ratio, which indirectly reflects the appearance of desensitization, is significant for the Ara h2 fraction ((p=0.03). (FIGS. 3 and 4).

TABLE 7

Effects of desensitization on the immunological balance

| | | FCT 1 m ± sd | p | Induction phase medium m ± sd (p*) | FCT 2 m ± sd (p**) | p** | p |
|---|---|---|---|---|---|---|---|
| Diameter of the reaction (mm) | Ara. | 12.4 ± 6.7 | ns | | 6.1 ± 4 (<0.0001) | | 0.58 |
| | Plac. | 12.5 ± 6.5 | | | 8 ± 3.8 (<0.05) | | |
| Total IgE (IU/mL) | Ara | 628 ± 469 | ns | 698 ± 411 (0.357) | 840 ± 573 (0.004) | | 0.014 |
| | Plac | 1266 ± 1504 | | 1193 ± 1511 (0.324) | 1175 ± 1591 (0.264) | | |
| Peanut Sp. IgE (IU/mL) | Ara | 62.5 ± 34.5 | ns | 76.0 ± 34.7 (0.001) | 78.6 ± 32.8 (<0.001) | | 0.044 |
| | Plac | 79.0 ± 30.7 | | 78.7 ± 32.9 (0.880) | 79.3 ± 32.1 (0.244) | | |
| Ara h1 SpIgE (IU/mL) | Ara | 33.4 ± 36.6 | ns | 38.1 ± 39.1 (0.227) | 41.6 ± 38.1 (0.011) | | 0.10 |
| | Plac | 33.6 ± 29.0 | | 31.3 ± 22.0 (0.421) | 28.95 ± 25.0 (0.924) | | |
| Ara h2 SpIgE (IU/mL) | Ara | 50.4 ± 35.9 | ns | 63.0 ± 35.6 (0.009) | 62.5 ± 35.0 (0.010) | | 0.25 |
| | Plac | 70.9 ± 34.2 | | 73.44 ± 36.03 (0.276) | 71.38 ± 36.85 (0.105) | | |
| Ara h3 SpIgE (IU/mL) | Ara | 24.8 ± 38.5 | ns | 32.43 ± 41.69 (0.160) | 31.12 ± 38.31 (0.084) | | 0.20 |
| | Plac | 23.9 ± 32.9 | | 23.7 ± 31.9 (0.881) | 21.3 ± 31.0 (0.528) | | |
| Ara h8 SpIgE (IU/mL) | Ara | 1.5 ± 5.2 | <0.01 | 1.2 ± 3.5 (0.451) | 2.2 ± 5.3 (0.272) | | 0.06 |
| | Plac | 17.6 ± 32.6 | | 19.8 ± 33.7 (0.421) | 24.3 ± 33.2 (0.126) | | |
| Ara h9 SpIgE (IU/mL) | Ara | 0.2 ± 0.7 | ns | 0.1 ± 0.4 (0.743) | 0.2 ± 0.7 (0.650) | | 0.38 |
| | Plac | 1.0 ± 1.6 | | 0.9 ± 1.5 (0.826) | 1.5 ± 2.8 (0.403) | | |
| Total IgG4 (mg/mL) | Ara | 0.86 ± 0.84 | ns | 0.85 ± 0.80 (0.217) | 0.93 ± 0.82 (0.240) | | 0.36 |
| | Plac | 0.83 ± 0.63 | | 0.88 ± 0.73 (0.429) | 0.78 ± 0.59 (0.348) | | |
| Peanut sp IgG4 (mg/mL) | Ara | 0.40 ± 0.45 | ns | 0.99 ± 0.85 (0.303) | 2.98 ± 3.69 (<0.001) | | 0.04 |
| | Plac | 0.44 ± 0.53 | | 0.50 ± 0.53 (0.458) | 0.42 ± 0.44 (0.797) | | |
| Ara h1 sp IgG4 (mg/mL) | Ara | 0.04 ± 0.05 | ns | 0.06 ± 0.07 (0.909) | 0.38 ± 0.89 (0.026) | | 0.12 |
| | Plac | 0.036 ± 0.04 | | 0.04 ± 0.05 (0.078) | 0.02 ± 0.02 (0.851) | | |
| Ara h2 sp IgG4 (mg/mL) | Ara | 0.09 ± 0.10 | ns | 0.31 ± 0.46 (0.627) | 1.46 ± 2.87 (0.003) | | 0.49 |
| | Plac | 0.08 ± 0.05 | | 0.10 ± 0.08 (0.002) | 0.07 ± 0.06 (0.490) | | |
| Ara h3 sp IgG4 (mg/mL) | Ara | 0.22 ± 0.40 | ns | 0.24 ± 0.33 (0.787) | 0.55 ± 0.53 (0.0001) | | 0.006 |
| | Plac | 0.08 ± 0.07 | | 0.12 ± 0.10 (0.004) | 0.09 ± 0.10 (0.288) | | |
| Ara h8 sp IgG4 (mg/mL) | Ara | 0.01 ± 0.03 | ns | 0.01 ± 0.04 (0.778) | 0.01 ± 0.058 (0.582) | | 0.029 |
| | Plac | 0.11 ± 0.18 | | 0.11 ± 0.15 (0.897) | 0.17 ± 0.24 (0.108) | | |
| Ara h9 sp IgG4 (mg/mL) | Ara | 0.04 ± 0.13 | ns | 0.06 ± 0.21 (0.849) | 0.20 ± 0.77 (0.146) | | 0.17 |
| | Plac | 0.34 ± 0.79 | | 0.26 ± 0.55 (0.218) | 0.3 ± 0.57 (0.275) | | |

Legend:
m ± sd = average ± mean standard deviation
Ara = peanut group or group treated by the capsule according to the invention
Plac = placebo group
sp = specific FIGS. 3 and 4 represent the progress of the IgG/IgE ratios during the build-up phase. In FIG. 3 (ratio of specific to peanut IgG4/IgE), we observe an increase (peanut=0.06) in the ratio of the IgG4 (μg/mL)/IgE antibodies (IU/mL) specific to peanut between FCT1 and FCT2. In FIG. 4, we observe a significant increase (p=0.03) of the ratio of the specific IgG4 (μg/mL)/IgE (IU/mL) antibodies of the Ara h2 fraction of peanut between FCT1 and FCT2.

7. CONCLUSION

The peanut capsule and its ingestion in closed (unopened) form according to the invention prevents contact between the peanut composition that it contains and the buccal mucosa for different reasons.

The first reason is that the buccal mucosa is rich in antigen-presenting cells: this exposes the patient to allergy risks or even anaphylactic shock and thus limits the possibilities of desensitization. Conversely, the inventors propose to expose the allergen by putting it into direct contact with the antigen-presenting cells of the small intestine which is the physiological site of the induction of oral tolerance to food antigens, in order to reduce the risks and intensity of allergy reactions during desensitization while maintaining therapeutic efficacy.

The second reason is that the buccal mucosa is the site of taste and partly of smell. Now peanut has a very characteristic smell and taste that are difficult to mask. Administering capsules with intestinal release prevents the nocebo effect, namely an effect where a patient assumes that the is in the process of consuming the allergic substance and triggers an allergy reaction.

The results of the double blind clinical trial show that the administration of the capsule according to the invention makes it possible, on the one hand, to rigorously measure the threshold of reactivity to the allergen by carrying out a double-blind placebo-controlled food challenge test and, on the other hand, to efficiently desensitize the treated patients while reducing the risks of the occurrence of allergy reactions among them, especially the risks of eosinophilic oesophagitis and anaphylactic shock.

An exemplary embodiment of the invention overcomes the drawbacks of the prior art, especially in terms of acceptability, efficiency and security by reducing side effects and/or adverse events.

More specifically, at least one embodiment provides a composition that can be used to desensitize and/or induce tolerance among peanut-allergic subjects.

An exemplary embodiment proposes a method for diagnosing an allergy in a subject.

An exemplary embodiment proposes a composition for exhaustively and definitively desensitizing a peanut-allergic subject.

An exemplary embodiment proposes a composition for use in a method for desensitizing and/or inducing tolerance in a peanut-allergic subject, while at the same time efficiently masking the taste, color and odor of peanut, thus eliminating food aversion to this allergen.

An exemplary embodiment proposes a composition for use in a method for desensitizing and/or inducing tolerance in a peanut-allergic subject, by reducing the side effects, especially the risk of oral-pharyngeal reactions (oral syndromes), eosinophilic oesophagitis, anaphylactic reactions and other adverse effects or events.

An exemplary embodiment proposes a method for making a composition for use in a method for desensitizing and/or inducing tolerance in a peanut-allergic subject, while minimizing the occurrence of the nocebo effect.

An exemplary embodiment proposes a composition intended for use in a method for desensitizing and/or inducing tolerance in a peanut-allergic subject aged 1 to 18 years.

Although the present disclosure has been described with reference to one or more examples, workers skilled in the art will recognize that changes may be made in form and detail without departing from the scope of the disclosure and/or the appended claims.

The invention claimed is:

1. A method for desensitizing and/or inducing tolerance and/or maintaining tolerance in a peanut-allergic subject, the method comprising:
   orally administering to the subject of at least one gastro-intestinal release capsule, said capsule comprising a shell and a core, said core comprising a peanut composition comprising peanuts, at least one oil, at least one first excipient being a pulverulent excipient, and, optionally, at least one second excipient being a pre-biotic excipient;
   wherein said capsule is provided to the subject in an unopened form and ingested in an unopened form and not mixed into an alimentary bolus.

2. The method according to claim 1, wherein the subject is 1 to 18 years of age or, aged 18 years or more.

3. The method according to claim 1, wherein said method comprises a phase of desensitizing and/or induction of a tolerogenic response of the immune system, followed by a phase of keeping up and/or maintaining the tolerance, wherein said phase of desensitizing and/or induction of a tolerogenic response of the immune system and said phase of keeping up and/or maintaining the tolerance occur concurrently with the step of administering.

4. The method according to claim 3, wherein the phase of desensitizing and/or induction of a tolerogenic response comprises daily administering of said at least one gastro-intestinal release capsule of an average dose of peanut increasing from 10 mg to 2 g during 20 to 28 weeks.

5. The method according to claim 3, wherein the phase of keeping up and/or maintaining tolerance comprises administering a daily average dose of peanut of 2 g to 5 g.

6. The method according to claim 3, wherein the phase of desensitizing and/or induction of a tolerogenic response comprises daily administering of said at least one gastro-intestinal release capsule of an average dose of peanut increasing from 10 mg to 2 g during 24 weeks.

7. The method according to claim 5, wherein the phase of keeping up and/or maintaining tolerance is implemented with subjects aged 1 to 18 years tolerating a cumulated dose of peanut of at least 2 g.

8. The method according to claim 1, wherein the peanuts are roasted and full-fat peanuts.

9. The method according to claim 1, wherein said peanut composition comprises 10 mg to 1000 mg of peanuts.

10. The method according to claim 1, wherein said peanut composition comprises 10 mg to 750 mg of peanuts.

11. The method according to claim 1, wherein said peanut composition comprises 10 mg to 500 mg of peanuts.

12. The method according to claim 1, wherein said peanut composition comprises 5% to 70% of peanuts relative to the total weight of said peanut composition.

13. The method according to claim 1, wherein said peanut composition comprises a proportion of allergen protein between 10% to 40%, relative to the total weight of said peanut composition.

14. The method according to claim 1, wherein said peanut composition comprises a proportion of allergen proteins between 10% to 30% relative to the total weight of said peanut composition.

15. The method according to claim 1, wherein said peanut composition comprises a proportion of allergen proteins between 15% to 25% relative to the total weight of said peanut composition.

16. The method according to claim 1, wherein said peanut composition comprises a proportion of allergen proteins Ara h1 between 10% to 15% relative to the total weight of the proteins of said peanut composition, a proportion of allergen proteins Ara h2 between 2% to 10% relative to the total weight of the proteins of said peanut composition and a proportion of allergen proteins of Ara h 3 between 10% to 20% relative to the total weight of the proteins of said peanut composition.

17. The method according to claim 1, wherein said at least one oil is a sunflower oil.

18. The method according to claim 1, wherein said pulverulent first excipient is tricalcium phosphate.

19. The method according to claim 16, wherein said pulverulent first excipient is chosen from among beta tricalcium phosphate, alpha tricalcium phosphate and their mixture.

20. The method according to claim 17, wherein said pulverulent first excipient is beta tricalcium phosphate or alpha tricalcium phosphate.

21. The method according to claim 1, wherein said prebiotic second excipient is lactose.

22. The method according to claim 19, wherein said prebiotic second excipient is lactose monohydrate.

23. The method according to claim 1, wherein said peanut composition comprises 20 mg to 315 mg of the pulverulent first excipient and 0 mg to 100 mg of the prebiotic second excipient.

24. The method according to claim 1, wherein said peanut composition comprises a proportion of said pulverulent first excipient between 15% to 55% of the total weight of the peanut composition.

25. The method according to claim 1, wherein said peanut composition comprises a proportion of said second excipient, between 10% to 75% of the total weight of said peanut composition.

26. A method of enabling diagnosis of a peanut allergy in a subject, said method comprising:
administrating to the subject at least one gastro-intestinal release capsule intended for oral use, said capsule comprising a shell and a core, said core comprising a peanut composition comprising peanut, at least one oil, at least one first excipient being a pulverulent excipient and, optionally, at least one second excipient being a prebiotic excipient, wherein said capsule is provided in an unopened form and ingested in an unopened form and not mixed into an alimentary bolus.

* * * * *